US010518260B1

(12) United States Patent
Zheng (10) Patent No.: US 10,518,260 B1
(45) Date of Patent: Dec. 31, 2019

(54) DEVICE FOR SEPARATION OF PLASMA OR SERUM FROM BLOOD CELLS AND METHODS OF USING THE DEVICE

(71) Applicant: NANO DISCOVERY, INC., Orlando, FL (US)

(72) Inventor: Tianyu Zheng, Orlando, FL (US)

(73) Assignee: NANO DISCOVERY, INC., Orlando, FL (US)

(*) Notice: Subject to any disclaimer, the term of this patent is extended or adjusted under 35 U.S.C. 154(b) by 0 days.

(21) Appl. No.: 16/422,703

(22) Filed: May 24, 2019

Related U.S. Application Data (60) Provisional application No. 62/841,604, filed on May 1, 2019, provisional application No. 62/846,862, filed on May 13, 2019.

(51) Int. Cl.
| | |
|---|---|
| G01N 35/00 | (2006.01) |
| G01N 33/48 | (2006.01) |
| G01N 33/86 | (2006.01) |
| B01L 3/00 | (2006.01) |
| G01N 33/49 | (2006.01) |

(52) U.S. Cl.
CPC .......... B01L 3/5023 (2013.01); G01N 33/491 (2013.01); G01N 33/4905 (2013.01); *B01L 2300/069* (2013.01); *B01L 2400/0406* (2013.01)

(58) Field of Classification Search
CPC .... B01L 3/5023; G01N 33/491; G01N 33/49; G01N 35/00; G01N 33/48; G01N 33/86
USPC ....... 422/50, 68.1, 502, 503; 436/43, 63, 66, 436/69
See application file for complete search history.

(56) References Cited

U.S. PATENT DOCUMENTS

| | | | | |
|---|---|---|---|---|
| 3,918,908 A | * | 11/1975 | Moyer | G01N 11/02 436/69 |
| 4,753,776 A | * | 6/1988 | Hillman | B01D 39/2017 210/451 |
| 5,064,541 A | * | 11/1991 | Jeng | B01D 39/00 210/295 |
| 7,927,810 B2 | | 4/2011 | Togawa et al. | |
| 9,283,313 B2 | | 3/2016 | Huemer | |

(Continued)

OTHER PUBLICATIONS

Basu, D. et al., "Overview of blood components and their preparation," *Indian Journal of Anaesthesia*, 2014, 58(5):529-537.

(Continued)

*Primary Examiner* — Brian J. Sines
(74) *Attorney, Agent, or Firm* — Saliwanchik, Lloyd & Eisenschenk (57) ABSTRACT

The invention pertains to a device for separation of serum or plasma from blood cells without application of an external force, such as centrifugation or pressure. The device comprises a hollow body having a top open end and a bottom end comprising a porous membrane. Particularly, the pore size of the porous membrane is between 10 nm and 20 µm. The invention also pertains to methods of separating serum or plasma from blood cells, the methods comprising introducing into the device a mixture of serum or plasma and blood cells and incubating the device in a substantially vertical position for between about one minute and thirty minutes to allow the separation of serum or plasma from blood cells under gravity.

10 Claims, 3 Drawing Sheets

(56) References Cited

U.S. PATENT DOCUMENTS

2006/0029923 A1* 2/2006 Togawa .............. B01D 61/18
  435/2
2016/0313298 A1* 10/2016 Wright .............. G01N 33/491

OTHER PUBLICATIONS

Mahajan, S., "Vacutainer and Their Use in Blood Sampling," *Med Care Tips Health & Medical Care*, Web page < https://medcaretips.com/vacutainer/>, 7 pages, retrieved from Internet Archive Wayback Machine <https://web.archive.org/web/20180528214123/https://medcaretips.com/vacutainer/> on May 28, 2018.

Hester, J. P. et al., "Principles of Blood Separation and Component Extraction in a Disposable Continuous-Flow Single-Stage Channel," *Blood*, Jul. 1979, 54(1):254-268, Grune & Stratton, Inc.

Lee, D., "A Blood Separation Device That Eliminates Centrifugation and Reduces Preanalytical Errors and Turnaround Times," *American Laboratory*, Feb. 9, 2018, pp. 1-5, 2019 CompareNetworks, Inc.

"seraSTAT® Rapid Blood Cell Separation," *Akers* Bio, Web page <http://www.akersbio.com/technology/serastat-rapid-blood-cell-separation>, 2 pages, retrieved from Internet on May 14, 2019, Akers Biosciences, Inc.

"HemaSpot-SE Blood Separation Device," *Spot On* Sciences, Web Page <http://www.spotonsciences.com/products/hemaspot-se/>, 7 pages, retrieved from Internet on May 14, 2019, Spot on Sciences.

"Minivette® POCT 200µl," Web Page <https://www.sarstedt.com/en/products/diagnostic/capillary-blood/tubes/product/17.2111.200/>, 7 pages, retrieved from Internet on May 14, 2019, SARSTEDT AG & Co. KG.

Liu, C. et al., "Membrane-Based, Sedimentation-Assisted Plasma Separator for Point-of-Care Applications," *Analytical Chemistry*, 2013, 85:10463-10470, American Chemical Society.

Vemulapati, S. et al., "H.E.R.M.E.S: rapid blood-plasma separation at the point-of-need†," *Lab on a Chip*, 2018, 18:3285-3292, The Royal Society of Chemistry.

* cited by examiner

DEVICE FOR SEPARATION OF PLASMA OR SERUM FROM BLOOD CELLS AND METHODS OF USING THE DEVICE

CROSS-REFERENCE TO RELATED APPLICATIONS

This application claims the benefit of U.S. Provisional Application Ser. Nos. 62/841,604, filed May 1, 2019; and 62/846,862, filed May 13, 2019; which are hereby incorporated by reference in their entirety.

BACKGROUND OF THE INVENTION

Whole blood contains red blood cells, white blood cells, platelets, clotting factors, and plasma. Aberrant levels of cellular and non-cellular components of blood can be used to detect or diagnose diseases. While some clinical tests are performed using whole blood, many blood tests use blood serum or plasma. Blood serum or plasma is typically obtained by centrifugation of blood. Serum is obtained by centrifuging whole blood following clotting, while plasma is obtained by centrifuging whole blood containing added anticoagulants.

The separation of serum or plasma from whole blood using centrifugation increases the turnaround time and requires the use of an electrical device. To perform diagnostic tests in point-of-care facilities or in underserved or budget-limited regions where electricity is unavailable or not easily accessible or centrifuge is unavailable or unaffordable, obtaining blood serum or plasma samples without the use of centrifuge or other electricity-powered devices is critical for providing healthcare.

Several centrifuge-free blood component separation devices are available. SeraSTAT® Rapid Blood Cell Separator (Akers Biosciences, Inc. West Deptford, N.J.) and HemaSpot™-SE Blood Separation Device (Spot On Sciences, Inc. Austin, Tex.) are two examples. SeraSTAT® rapid blood cell separator requires the use of blood component-specific agents in the filtration membrane. A blood sample enters from one side of the membrane and, after passing through the membrane, the cell-free blood components are collected at the opposite side of the membrane. The blood flows under an applied pressure, not under gravity.

HemaSpot™-SE blood separation device separates soluble components in the blood from blood cells and platelets based on their size-dependent flow speed through a horizontal, spiral-shaped flow channel. Liu et al. reported a small sized filtration device for plasma blood sample collection via a size-exclusion membrane. This device contains a two-chamber container separated by a size exclusion membrane. Blood sample is injected into one chamber and plasma is collected from another chamber after diffusing through the size exclusion membrane. Vemulapati et al. designed a device for plasma collection using functionalized magnetic beads to capture red blood cells and separate the red blood cells from the rest of the blood components. The U.S. Pat. No. 7,927,810 discloses a device for separation of plasma or serum from the blood cells using a filtration membrane having a certain porosity. Such device allows whole blood to pass through the membrane. By applying pressure from the top end of the device, blood plasma or serum is collected from the bottom of the container after flowing through the membrane.

BRIEF SUMMARY OF THE INVENTION

Certain embodiments of the invention provide devices for separation of serum or plasma from blood cells without application of an external force, such as centrifugal force or pressure. The device disclosed herein comprises a hollow body having a top open end and a bottom end comprising a porous material. The porous material can be a membrane, disc, rod, polymer gel, polymer beads, or sponge. The porous material has pores having the largest pore size smaller than about 20 µm. Particularly, the pore size of the porous material is between 10 nm and 20 µm. The pore size of the porous material inhibits the blood cells from passing through the material and, thus, physically supports the cells that settle on the porous material.

Additional embodiments of the invention provide methods of separating serum or plasma from cells, the methods comprising introducing into the device disclosed herein a mixture comprising serum or plasma and blood cells and incubating the device in a substantially vertical position for at least about one minute to about thirty minutes to allow the cells to settle under gravity thereby separating the serum or plasma from the cells. In preferred embodiments, the methods disclosed herein are used to separate whole blood into serum or plasma and blood cells.

DETAILED DESCRIPTION OF THE INVENTION

Disclosed herein are devices and methods for separation of serum or plasma from cells, particularly, blood cells, without applying any external force, such as centrifugal force or pressure.

"An external force" as used herein refers to any force other than gravitation force. Therefore, an external force includes centrifugal force applied to a blood sample being centrifuged or pressure, for example, vacuum pressure or pressure through a plunger, applied to a blood sample being forced through a membrane, such as a filter. Additional examples of an external force are well-known or would be readily apparent to a person of ordinary skill in the art.

Figure 1:
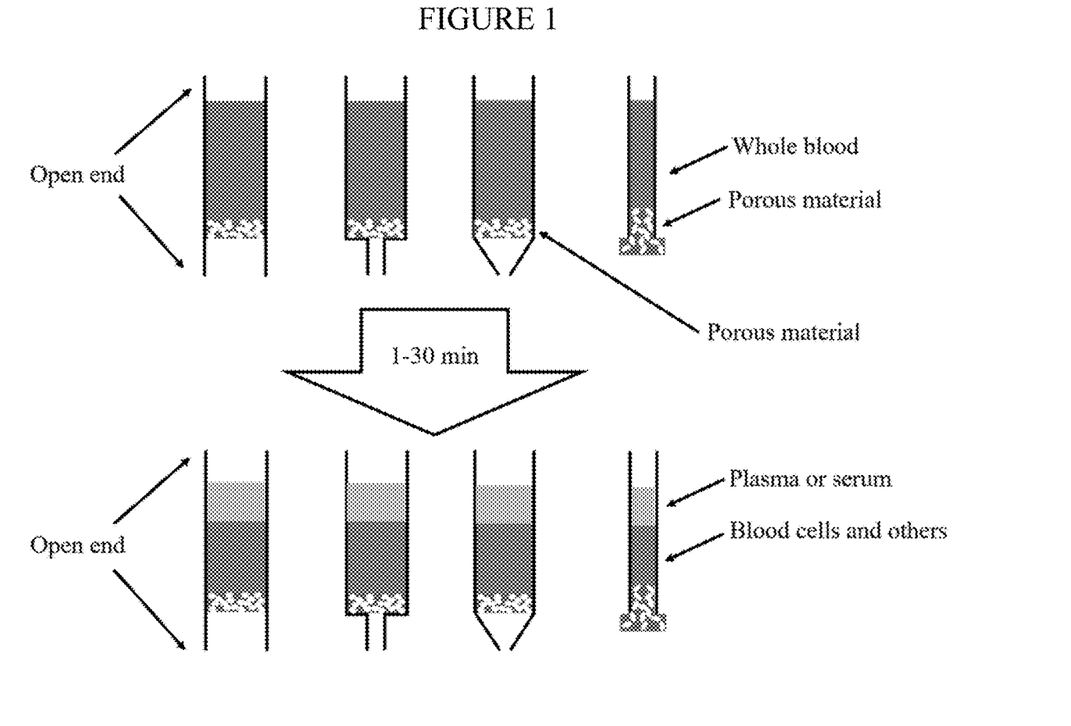
FIG. 1. Schematic representation of the devices disclosed herein for separating blood serum or plasma from blood cells.

FIG. 1 is an illustration of one example of the device disclosed herein. In certain embodiments, this device comprises a column or tube or container with two ends. One end of the container has a porous material and the other end of the container is an open end that can receive a mixture of serum or plasma and blood cells, such as whole blood.

When serum or plasma is separated from cells using this device, the device is incubated with the open end towards the top and the end containing the porous material towards the bottom. The porous material can be at the bottom end or distal from the bottom end. Preferably, the porous material is in the lower half of the hollow body. Therefore, the open end is also referenced herein as the top end and the end containing the porous material is also referenced herein as the bottom end. The blood cells settle on the porous material under gravity.

To use the device provided in FIG. 1, the blood from a subject is introduced into the device from the open end, for example, by direct dropping or capillary force. Accordingly, in certain embodiments, the hollow body of the device is in the form of a capillary tube. The hollow body of the device that is in the form of a capillary tube has an internal diameter of between 0.5 and 5 mm, preferably, between 1 and 4 mm, ever more preferably, between 2 and 3 mm, and most preferably, about 2.5 mm. Therefore, in certain embodiments, the blood from a subject is introduced into the device by capillary force of the hollow body of the device that is in the form of a capillary tube.

The device is then placed in a substantially upright position, i.e., with the open end towards the top and the end containing the porous material towards the bottom. The device is incubated in the substantially upright position for a certain period of time, typically for at least between about 1 minute and about 30 minutes.

During this incubation, blood cells and other large particles settle towards the bottom and are trapped by the porous material, while the serum or plasma portion remains as the top layer closer to the open end of the device. Unlike other filtration-based blood separation devices, in the devices disclosed herein the serum or plasma does not flow through the porous material or substantially flow through the porous material and, thus, is not collected from the bottom end of the device. In the devices disclosed herein, the porous material inhibits pressure built-up in the devices when blood cells precipitate towards the bottom of the devices. Also, the porous material inhibits blood cells from passing through. The pore size of the porous material is designed such that the material does not allow significant amount of blood serum or plasma to pass through; however, a small amount of serum or plasma, for example, up to about 20% of the entire serum or plasma in a sample, may enter into the porous material. However, the entirety of the serum or plasma will not leak through the entire porous material.

Figure 2A:
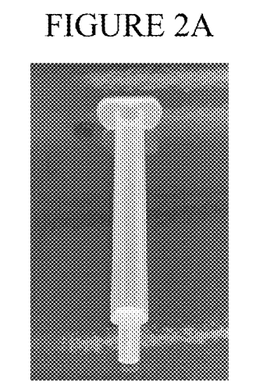
FIGS. 2A-2C. 2A and 2B. Two examples of the devices disclosed herein. 2C. Blood serum sample separated from blood cells using the device of FIG. 2B.
Figure 2B:
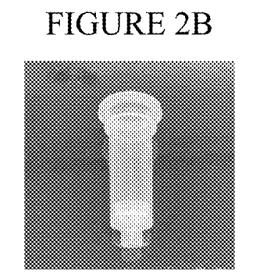
Figure 2C:
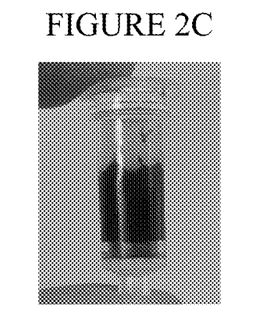
Figure 3:
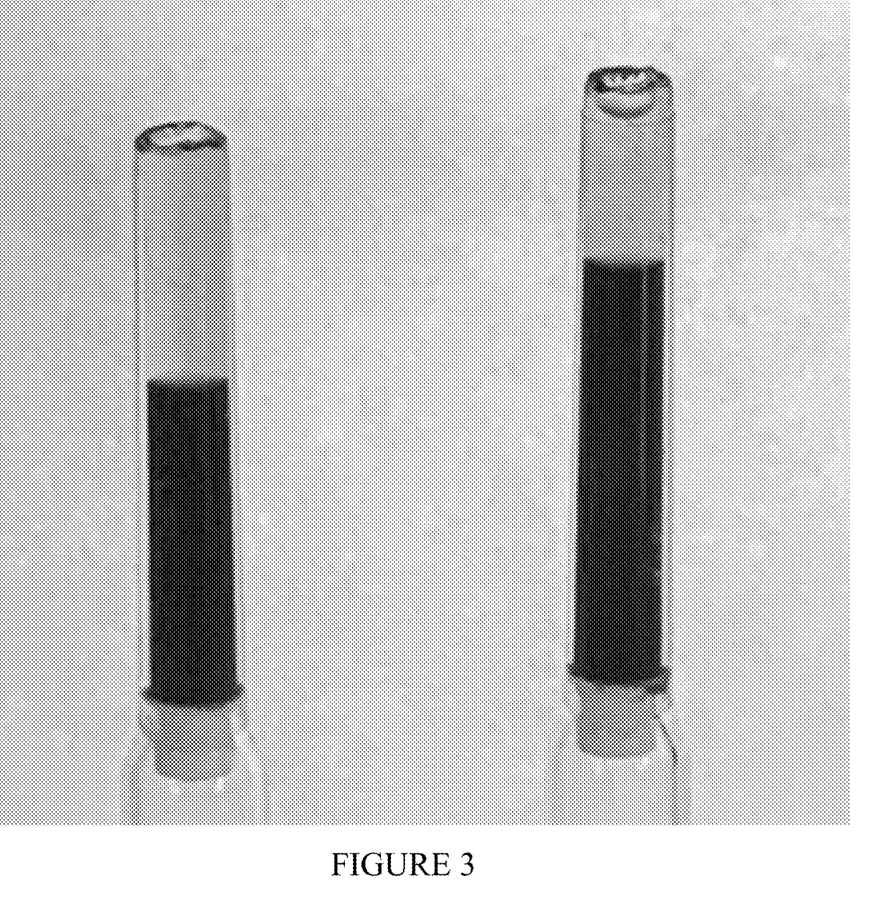
FIG. 3. An example of the device disclosed herein demonstrating the separation of blood plasma from whole blood.

Importantly, the pore size of the porous material is designed such that these pores are not clogged by blood cells or other particles in blood serum or plasma, and that these pores do not allow red blood cells or stacked red blood cells to pass through the material. FIG. 2C is an illustration of a blood serum sample separated using the device of FIG. 2B.

Accordingly, the disclosure provides a device comprising: a hollow body having a first end and a second end, the first end configured to receive a mixture of plasma or serum and blood cells and the second end comprising a porous material, wherein the porous material has a pore size smaller than about: 20 µm, 19 µm, 18 µm, 17 µm, 16 µm, 15 µm, 14 µm, 13 µm, 12 µm, 11 µm, or 10 µm.

In preferred embodiments, the interior of the hollow body is in fluid communication with exterior air through both the first end and the second end. The phrase "hollow body is in fluid communication with exterior air" indicates that before a sample is introduced into the device, air can flow freely from the first end and the second end and through the hollow body. In other words, before a sample is introduced into the device, the air pressure in the hollow body and outside the two ends of the device is identical. After a sample is introduced into the device, the sample would prevent the free exchange of air from the first end and the second end and through the hollow body.

The hollow body serves as a container for a mixture of serum or plasma and blood cells. Therefore, the hollow body can be made from any material that provides an appropriate enclosure for a mixture of serum or plasma and blood cells. Such materials include, but are not limited to, a plastic, glass, or metal.

Suitable plastic materials include polypropylene, polycarbonate, polyacrylics, polyethylene, and polystyrene. Additional plastic materials are known in the art and such embodiments are within the purview of the invention.

In certain embodiments, the hollow body is coated on the inside with an anti-coagulant, such as EDTA, sodium citrate, or heparin. The anti-coagulant may also be added to the porous material. Additional anticoagulants are known in the art and such embodiments are within the purview of the invention.

In further embodiments, clotting activators may be added to the device to facilitate clotting of the blood and separation of serum. The clotting activators may be added to the porous material, coated on the inner wall of the hollow body, or both. Non-limiting examples of the clotting activators include thrombin, silica and silicate clot activators, ficolin-1, and ficolin-2. Additional examples of clotting activators are known to a person of ordinary skill in the art and such embodiments are within the purview of the invention.

In further embodiment, reagents may be added to the device to facilitate the red blood cells to form rouleaux and accelerate the sedimentation of red blood cells to the bottom of the device. Example of such reagents includes dextran polymers.

In further embodiments, reagents may be added to the device to accelerate clot retraction time. By accelerating clot retraction, more serum can be obtained within a shorter time of incubation. Such reagents may be added to the porous material, coated on the inner wall of the hollow body, or both. Non-limiting examples of the clot retraction activators include thrombin and adenosine diphosphate (ADP). Additional examples of clot retraction accelerators are known to a person of ordinary skill in the art and such embodiments are within the purview of the invention.

The porous material can be made from nylon, polyethylene, cellulose, cellulose acetate, polyvinylidene difluoride (PVDF), nitrocellulose or other polymeric or non-polymeric materials. Different pore sizes of the porous material can be designed to optimize the separation of plasma or serum from blood cells obtained from different animals. Particularly, the pore size of a material can be determined based on the size of the red blood cells of an animal whose serum or plasma is to be separated from the blood cells.

Preferably, the largest pore size of the porous material is smaller than the smallest size of red blood cells of an animal whose blood is to be separated into serum or plasma and blood cells. For example, human red blood cells are between 6 µm and 8 µm in diameter. Therefore, in certain embodiments, the pore size of the porous material in the device disclosed herein has a size smaller than 6 µm. The size of red blood cells in many other animals is known in the art and a person of ordinary skill in the art can produce a device suitable for separation of serum or plasma from the blood cells in bloods from such animals.

In certain embodiments, the pore size of the porous material is: between 10 nm and 20 µm; between 100 nm and 19 µm, between 100 nm and 18 µm, between 100 nm and 17 µm, between 100 nm and 16 µm, between 100 nm and 15 µm, between 100 nm and 14 µm, between 100 nm and 13 µm, between 100 nm and 12 µm, between 100 nm and 11 µm, between 100 nm and 10 µm, between 200 nm and 10 µm, 200 nm and 8 µm, 200 nm and 6 µm, 200 nm and 4 µm, 200 nm and 2 µm, between 500 nm and 10 µm, between 500 nm and 8 µm, between 500 nm and 6 µm, between 1 µm and 10 µm, between 1 µm and 8 µm, between 2 µm and 7 µm, between 3 µm and 6 µm, or between 4 µm and 5 µm.

Preferably, the porous material is free from or substantially free from pores having a size outside the stated range. For example, the porous material has less than 40%, less than 30%, less than 20%, less than 10%, less than 5%, less than 3%, or less than 1% of the pores that have a size outside the stated range.

Accordingly, in certain embodiments, at least 99%, at least 97%, at least 95%, at least 90%, at least 80%, at least 70%, or at least 60% of the pores in the porous membrane have a size: between 10 nm and 20 µm; between 100 nm and 19 µm, between 100 nm and 18 µm, between 100 nm and 17 µm, between 100 nm and 16 µm, between 100 nm and 15 µm, between 100 nm and 14 µm, between 100 nm and 13 µm, between 100 nm and 12 µm, between 100 nm and 11 µm, between 100 nm and 10 µm, between 200 nm and 10 µm, 200 nm and 8 µm, 200 nm and 6 µm, 200 nm and 4 µm, 200 nm and 2 µm, between 500 nm and 10 µm, between 500 nm and 8 µm, between 500 nm and 6 µm, between 1 µm and 10 µm, between 1 µm and 8 µm, between 2 µm and 7 µm, between 3 µm and 6 µm, or between 4 µm and 5 µm.

In additional embodiments, at least 99%, at least 97%, at least 95%, at least 90%, at least 80%, at least 70%, or at least 60% of the pores in the porous membrane have a size: between 10 nm and 20 µm; between 100 nm and 19 µm, between 100 nm and 18 µm, between 100 nm and 17 µm, between 100 nm and 16 µm, between 100 nm and 15 µm, between 100 nm and 14 µm, between 100 nm and 13 µm, between 100 nm and 12 µm, between 100 nm and 11 µm, between 100 nm and 10 µm, between 200 nm and 10 µm, 200 nm and 8 µm, 200 nm and 6 µm, 200 nm and 4 µm, 200 nm and 2 µm, between 500 nm and 10 µm, between 500 nm and 8 µm, between 500 nm and 6 µm, between 1 µm and 10 µm, between 1 µm and 8 µm, between 2 µm and 7 µm, between 3 µm and 6 µm, or between 4 µm and 5 µm.

The porous material may contain additives to facilitate the separation, clotting, or anticlotting of the blood.

The device may be used as a standalone device or a device for blood collection as well as processing. To combine blood collection and/or processing, the device disclosed herein may also be incorporated into another device for blood collection and/or a diagnostic device to further test the serum, plasma, or blood cells. For example, the device disclosed herein can be incorporated into a microfluidic device, a lateral flow immunoassay device, or other diagnostic test devices where serum or plasma sample is analyzed for an analyte, such as for the presence of an antibody or antigen.

When the device disclosed herein is used in conjunction with another device for blood collection, the open end of the hollow body can be modified to connect with the blood collection device, for example, a needle or a receiver that would engage with a dispenser from the blood collection device. In some embodiments, a blood collection device comprises a capillary tube, which can be used to collect small amount of blood through capillary effect. In other embodiments, a blood collection device comprises a needle and syringe to obtain blood from a subject. Additional embodiments of blood collection devices that can be used or attached to the device disclosed herein are known to a person of ordinary skill in the art and such embodiments are within the purview of the invention.

Further embodiments of the invention provide a method of separating serum or plasma from blood cells. The methods disclosed herein comprise introducing a mixture of serum or plasma and blood cells into the device disclosed herein, incubating the device for at least between about 1 minute and about 30 minutes to allow separation of the serum or plasma from the blood cells. The separated serum or plasma can then be aspirated from the device.

In preferred embodiments, the methods comprise separating whole blood into serum or plasma and blood cells. Whole blood samples can be collected using another device such as a syringe or a capillary and then introduced into the device disclosed herein.

Certain embodiments of the invention provide determining a property of blood or a blood component, the blood component separated using the devices and the methods disclosed herein. For example, blood hematocrit level can be determined using the devices and the methods of the invention. Similarly, blood cell sedimentation rate, such as erythrocyte sedimentation rate, or a blood clotting property can also be determined.

Accordingly, certain methods of the invention comprise introducing a blood sample into a device of the subject invention, incubating the device for at least between about 1 minute and about 30 minutes to allow separation of the serum or plasma, and measuring a property of the blood or a property of a blood component.

If the measured property of the blood is hematocrit, the device is incubated with a blood sample containing an anti-coagulant until the blood cells are separated from the plasma. In such embodiments, the device having a hollow body in the form of a capillary tube can be used.

If the measured blood property is erythrocyte sedimentation rate, the device is incubated with a blood sample containing an anti-coagulant until the blood cells are separated from the plasma. The erythrocyte sedimentation rate can be calculated based on the time required for the erythrocytes to sediment to a certain position of the device, or calculated based on the distance between the top of the clear plasma layer and the top of the erythrocyte layer.

To measure a blood clotting property, the device is incubated with a blood sample without an anti-coagulant until the blood is clotted. The clotting properties can be calculated based on, for example, the time required for the clotting or the amount of serum produced upon clotting.

The advantages of the devices and methods disclosed herein for separating serum or plasma from blood cells include, but are not limited to, the following: The devices and the methods disclosed herein do not require the use of a centrifuge. The devices and the methods disclosed herein do not require subjecting a sample to any external forces, such as pressure or centrifugal force. Absence of such external force protects the blood cells from physical damage, such as hemolysis. After collection of a blood sample and introduction of the blood into the devices disclosed herein, the methods disclosed herein do not require additional labor to separate serum or plasma from the blood cells because the methods simply involve incubating the device for a period of time. The devices disclosed herein can be easily incorporated into other diagnostic devices. The devices disclosed herein are of substantially lower costs compared to some of the commercially available devices. Therefore, the devices and the methods disclosed herein are suitable in situations and fields of limited finances and resources.

Definitions

As used herein, the singular forms "a," "an," and "the" are intended to include the plural forms as well, unless the context clearly indicates otherwise. To the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof)

"comprising," "comprises," and "comprise;" "consisting essentially of" and "consists essentially of;" and "consisting" and "consists" can be used interchangeably though each retains its traditional legal meaning.

The phrases "consisting essentially of" or "consists essentially of" indicate that the relevant description or claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Typically, the term "about" indicates that the relevant parameter is within the range of 0 to 20%, 0 to 10%, 0 to 5%, or 0 to 1% of a given value. For example, in the context of the incubation time of a blood sample, the incubation time includes the stated duration with a variation (error range) of 0-10% around the stated value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are intended to be explicitly included.

A "subject" refers to an animal, such as a mammal, for example a human. The methods described herein can be useful in both humans and non-human animals. Non-limiting examples of a subject include humans, non-human primates, bovine, porcine, canine, rodent, or feline animals. The devices and the methods disclosed herein can also be used to analyze serum or plasma and blood cells of non-mammalian animals, such as, birds, reptiles, etc., and such embodiments are within the purview of the invention.

Certain examples of the devices and the methods disclosed herein are described in the following embodiments:

Embodiment 1

A device comprising: a hollow body having a first end and a second end, the first end configured to receive a mixture of plasma or serum and blood cells and the second end comprising a porous material, wherein the porous material has a pore size smaller than about 20 μm.

Embodiment 2

The device of embodiment 1, wherein the pore size of the porous material is: between 10 nm and 20 μm; between 100 nm and 19 μm, between 100 nm and 18 μm, between 100 nm and 17 μm, between 100 nm and 16 μm, between 100 nm and 15 μm, between 100 nm and 14 μm, between 100 nm and 13 μm, between 100 nm and 12 μm, between 100 nm and 11 μm, between 100 nm and 10 μm, between 200 nm and 10 μm, 200 nm and 8 μm, 200 nm and 6 μm, 200 nm and 4 μm, 200 nm and 2 μm, between 500 nm and 10 μm, between 500 nm and 8 μm, between 500 nm and 6 μm, between 1 μm and 10 μm, between 1 μm and 8 μm, between 2 μm and 7 μm, between 3 μm and 6 μm, or between 4 μm and 5 μm.

Embodiment 3

The device of embodiment 2, wherein the porous material has less than 40%, less than 30%, less than 20%, less than 10%, less than 5%, less than 3%, or less than 1% of the pores that have a size outside the stated range.

Embodiment 4

The device of any of the preceding embodiments, wherein at least 60%, at least 70%, at least 80%, at least 90%, at least 95%, at least 97%, or at least 99% of the pores in the porous material have a size: between 10 nm and 20 μm; between 100 nm and 19 μm, between 100 nm and 18 μm, between 100 nm and 17 μm, between 100 nm and 16 μm, between 100 nm and 15 μm, between 100 nm and 14 μm, between 100 nm and 13 μm, between 100 nm and 12 μm, between 100 nm and 11 μm, between 100 nm and 10 μm, between 200 nm and 10 μm, 200 nm and 8 μm, 200 nm and 6 μm, 200 nm and 4 μm, 200 nm and 2 μm, between 500 nm and 10 μm, between 500 nm and 8 μm, between 500 nm and 6 μm, between 1 μm and 10 μm, between 1 μm and 8 μm, between 2 μm and 7 μm, between 3 μm and 6 μm, or between 4 μm and 5 μm.

Embodiment 5

The device of any of the preceding embodiments, wherein the porous material comprises nylon, polyethylene, cellulose, cellulose acetate, polyvinylidene difluoride (PVDF), or nitrocellulose.

Embodiment 6

The device of any of the preceding embodiments, wherein the hollow body comprises a plastic, glass, or metal.

Embodiment 7

The device of embodiment 6, wherein the plastic comprises polypropylene, polycarbonate, polystyrene, polyacrylics, or polyethylene.

Embodiment 8

The device of any of the preceding embodiments, wherein the hollow body is coated on the inside with an anti-coagulant or a clotting activator or a rouleaux formation accelerator.

Embodiment 9

The device of embodiment 8, wherein the anti-coagulant is EDTA, sodium citrate, or heparin.

Embodiment 10

The device of embodiment 8, wherein the clotting activator is thrombin, silica or silicate clotting activator, ficolin-1, or ficolin-2.

Embodiment 11

The device of embodiment 8, wherein the rouleaux formation accelerator is dextran polymer.

Embodiment 12

The device of any of the preceding embodiments, wherein the porous material comprises an anti-coagulant or a clotting activator or a rouleaux formation accelerator.

Embodiment 13

The device of embodiment 12, wherein the anti-coagulant is EDTA, sodium citrate, or heparin.

Embodiment 14

The device of embodiment 12, wherein the clotting activator is thrombin, silica or silicate clot activator, ficolin-1, or ficolin-2.

Embodiment 15

The device of embodiment 12, wherein the rouleaux formation accelerator is dextran polymer.

Embodiment 16

The device of any of the preceding embodiments, further comprising a device for blood collection and/or a diagnostic device to test serum, plasma, or blood cells.

Embodiment 17

The device of any of the preceding embodiments, wherein the hollow body and/or the porous material comprises a clot retraction activator.

Embodiment 18

The device of embodiment 17, wherein the clot retraction activator is thrombin or adenosine diphosphate.

Embodiment 19

A method of separating serum or plasma from blood cells, the method comprising:
i) providing a device of any of the preceding embodiments,
ii) introducing a mixture of serum or plasma and blood cells into the device,
iii) incubating the device for at least between about 1 minute and about 30 minutes to allow separation of the serum or plasma from the blood cells.

Embodiment 20

The method of embodiment 19, comprising separating the serum or plasma from the device.

Embodiment 21

The method of embodiment 19 or 20, wherein the blood is from a human, non-human primate, bovine, porcine, canine, rodent, feline, avian, or reptilian animal.

Embodiment 22

A method for determining a property of a blood or a blood component, comprising:
i) providing a device of any of embodiments 1 to 18,
ii) introducing the blood into the device,
iii) incubating the device for at least between about 1 minute and about 30 minutes to allow separation of the serum or plasma from the blood cells, and
iv) measuring the property of the blood or the blood component.

Embodiment 23

The method of embodiment 22, wherein the property of the blood is hematocrit, and wherein the method comprises incubating the device with a blood containing an anti-coagulant until the blood cells are separated from the plasma and measuring the hematocrit.

Embodiment 24

The method of embodiment 22, wherein the property of the blood is erythrocyte sedimentation rate, and wherein the method comprises incubating the device with a blood containing an anti-coagulant until the blood cells are separated from the plasma and measuring the erythrocyte sedimentation rate.

Embodiment 25

The method of embodiment 22, wherein the property of the blood is a blood clotting property, and wherein the method comprises incubating the device with a blood sample without an anti-coagulant until the blood is clotted and measuring the blood clotting property.

Embodiment 26

The method of embodiment 25, wherein the blood clotting property is the time required for the blood clotting or the amount of serum produced upon the blood clotting.

All patents, patent applications, provisional applications, and publications referred to or cited herein are incorporated by reference in their entirety, including all figures and tables, to the extent they are not inconsistent with the explicit teachings of this specification.

REFERENCES

1. Basu, D.; Kulkarni, R. Overview of Blood Components and Their Preparation. Indian J Anaesth. 2014 September-October; 58(5): 529-537.
2. World-wide-website: medcaretips.com/vacutainer/
3. Hester J. P.; Kellogg, R. M.; Mulzet, A. P.; Kruger, V. R.; McCredie, K. B.; Freireich E. J. Principle of Blood Separation and Component Extraction in a Disposable Continuous-Flow Single-Stage Channel. Blood, 1979, 54, 254-268.
4. World-wide web site: americanlaboratory.com/914-Application-Notes/347011-A-Blood-Separation-Device-That-Eliminates-Centrifugation-and-Reduces-Preanalytical-Errors-and-Turnaround-Times/
5. World-wide web site: akersbio.com/technology/serastat-rapid-blood-cell-separation
6. World-wide website: spotonsciences.com/products/hemaspot-se/

7. Liu, et al. Membrane-Based, Sedimentation-Assisted Plasma Separator for Point-of-Care Applications. Anal. Chem., 2013, 85 (21), pp 10463-10470.
8. Vemulapati, S.; Erickson, D. H.E.R.M.E.S: rapid blood-plasma separation at the point-of-need. Lab Chip. 2018, 18, 3285-3292.
9. U.S. Pat. No. 7,927,810.

The invention claimed is:

1. A method of separating a blood sample into serum or plasma and blood cells, the method comprising:
   i) providing a device comprising: a hollow body having a first end and a second end, the first end configured to receive the blood sample and the second end comprising a porous material, wherein an interior of the hollow body is in fluid communication with exterior air through both the first end and the second end,
   ii) introducing the blood sample into the device from the first end, and
   iii) incubating the device in a substantially vertical position, wherein the first end is towards the top and the second end is towards the bottom of the hollow body, for at least between about 1 minute and about 30 minutes to allow separation of the serum or plasma from the blood cells, wherein upon incubation the serum or plasma separates from the blood cells and forms a top layer towards the first end of the hollow body and the blood cells form a bottom layer towards the second end of the hollow body.

2. The method of claim 1, wherein the porous material of the device has a pore size smaller than about 20 μm.

3. The method of claim 1, wherein the hollow body and/or the porous material of the device comprises an anti-coagulant, a clotting activator, a rouleaux formation accelerator, or a clot retraction activator.

4. The method of claim 1, comprising aspirating the serum or plasma from the device.

5. The method according to claim 1, further comprising:
   iv) measuring the property of the blood or the blood component.

6. The method of claim 5, wherein the hollow body and/or the porous material of the device comprises an anti-coagulant, a clotting activator, a rouleaux formation accelerator, or a clot retraction activator.

7. The method of claim 5, wherein the property of the blood is:
   i) hematocrit, wherein the method comprises incubating the device with the blood sample until the blood cells are separated from the plasma, and measuring the hematocrit;
   or
   ii) erythrocyte sedimentation rate, wherein the method comprises incubating the device with the blood sample until the blood cells are separated from the plasma, and measuring the erythrocyte sedimentation rate.

8. The method of claim 5, wherein the property of the blood is a blood clotting property, wherein the method comprises incubating the device with the blood sample until the blood is clotted and measuring the blood clotting property.

9. The method of claim 8, wherein the blood clotting property is the time required for the blood clotting or the amount of serum produced upon the blood clotting.

10. The method of claim 1, further comprising collecting from the first end of the hollow body serum or plasma from the top layer.

* * * * *